(12) United States Patent
Van Der Mark et al.

(10) Patent No.: US 9,398,877 B2
(45) Date of Patent: Jul. 26, 2016

(54) METHOD AND DEVICE FOR OPTICAL IMAGING OF A TURBID MEDIUM

(75) Inventors: Martinus Bernardus Van Der Mark, Eindhoven (NL); Michael Cornelis Van Beek, Eindhoven (NL); Levinus Pieter Bakker, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 2446 days.

(21) Appl. No.: 12/094,670

(22) PCT Filed: Nov. 17, 2006

(86) PCT No.: PCT/IB2006/054317
§ 371 (c)(1),
(2), (4) Date: May 22, 2008

(87) PCT Pub. No.: WO2007/060586
PCT Pub. Date: May 31, 2007

(65) Prior Publication Data
US 2008/0300472 A1    Dec. 4, 2008

(30) Foreign Application Priority Data
Nov. 23, 2005   (EP) .................................. 05111185

(51) Int. Cl.
*A61B 5/1455*     (2006.01)
*A61B 5/00*       (2006.01)

(52) U.S. Cl.
CPC ............. *A61B 5/4312* (2013.01); *A61B 5/0091* (2013.01); *A61B 5/14551* (2013.01); *A61B 5/1455* (2013.01)

(58) Field of Classification Search
CPC ............. A61B 5/14551; A61B 5/4312; A61B 5/0091; A61B 5/1455
USPC .................... 600/475, 477, 479, 310; 424/9.1
See application file for complete search history.

(56) References Cited

U.S. PATENT DOCUMENTS 4,805,623 A * 2/1989 Jobsis ........................... 600/328
5,465,718 A * 11/1995 Hochman et al. ............. 600/420
(Continued)

FOREIGN PATENT DOCUMENTS

EP         0913120 A1    5/1999
WO    WO9620638 A1    7/1996
(Continued)

OTHER PUBLICATIONS

Kenneth T. Kotz, Konstantinos S. Kalogerakis, William N. Boenig, Khalid Amin and Gregory W. Faris, "Dynamic imaging of tumor vasculature in rodents: carbogen-induced contrast enhancement", Proc. SPIE 5312, 273 (2004).*

(Continued)

*Primary Examiner* — Long V Le
*Assistant Examiner* — Helene Bor

(57) ABSTRACT

Disclosed is a method and a device for optical imaging of a turbid medium. This method comprises a reference measurement of reference intensities of light emanating from the turbid medium at a reference blood oxygen saturation (SaO2) in the turbid medium and a reference imaging step for reconstructing a reference image of the turbid medium from the measured reference intensities. Furthermore the method comprises a contrast measurement of the contrast intensity of the light emanating from the turbid medium at a contrast blood oxygen saturation (SaO2) level in the turbid medium and a contrast imaging step for reconstructing a contrast image of the turbid medium from the measured contrast intensities. A comparison is made between the contrast image to the reference image of the turbid medium.

10 Claims, 3 Drawing Sheets

(56) References Cited

U.S. PATENT DOCUMENTS

Figure 1:
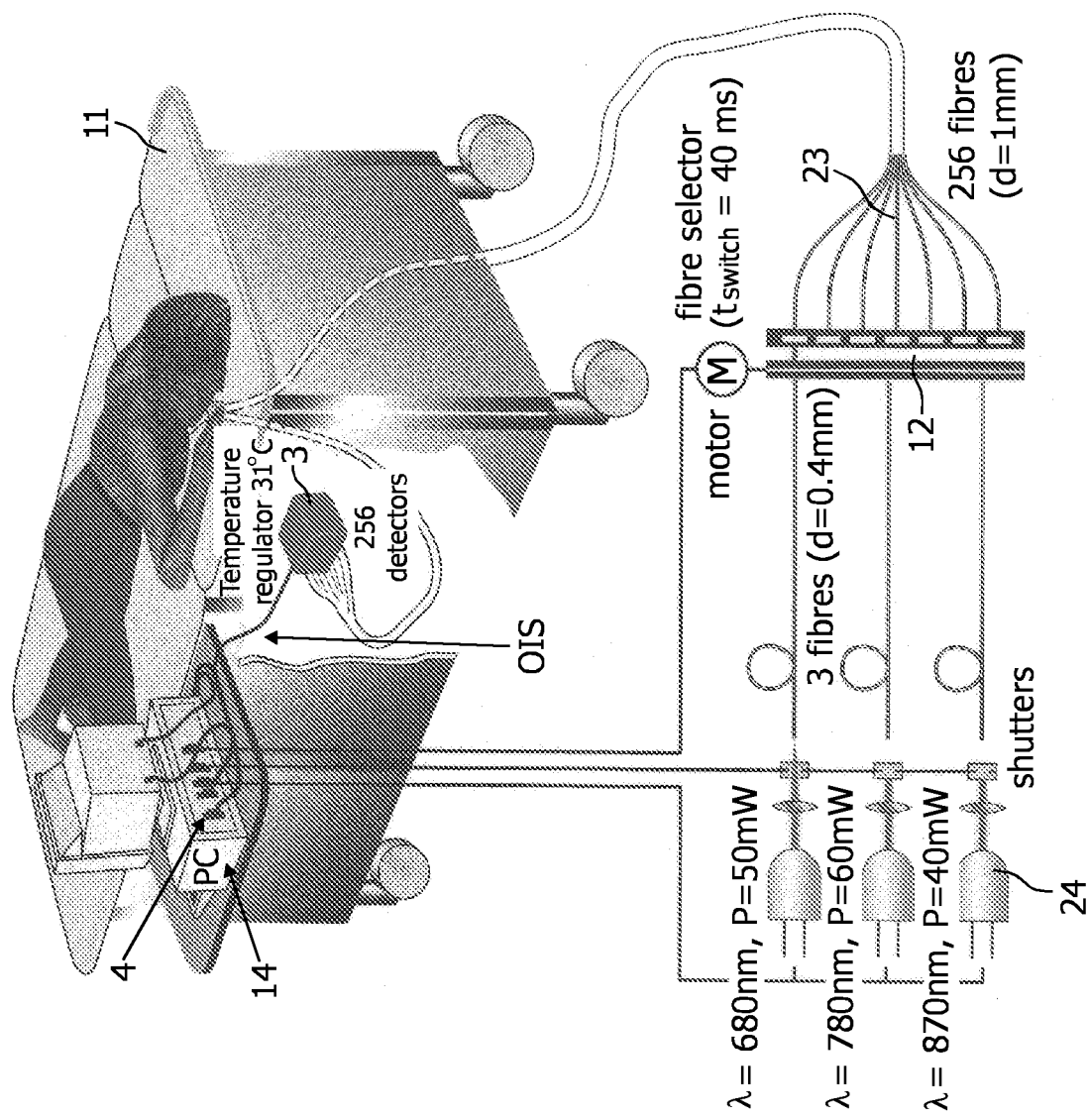

| | | | | |
|---|---|---|---|---|
| 5,699,789 | A | * | 12/1997 | Hendricks ............... 128/203.15 |
| 6,516,214 | B1 | * | 2/2003 | Boas ........................... 600/431 |
| 6,795,195 | B1 | | 9/2004 | Barbour et al. |
| 2007/0287897 | A1 | * | 12/2007 | Faris ............................ 600/310 |

FOREIGN PATENT DOCUMENTS

| | | |
|---|---|---|
| WO | WO0056206 A1 | 9/2000 |
| WO | 0174238 A1 | 10/2001 |
| WO | 2005070470 A1 | 8/2005 |

OTHER PUBLICATIONS

Howe et al. Issues in flow and oxygenation dependent contrast (FLOOD) imaging of tumours. NMR Biomedicine. (2001); 14:497-506.*

Delaey et al. A Retinal-Derived Relaxing Factor Mediates the Hypoxic Vasodilation of Retinal Arteries. Invest. Ophthalmol. Vis. Sci. Oct. 2000 vol. 41 No. 11 3555-3560.*

Hackett et al: "High Altitude Illness"; New England Journal of Medicine, vol. 345, No. 2, July 12, 2001, pp. 107-114.

Hampson, N.: "Pulse Oximetry in Severe Carbon Monoxide Poisoning"; The Cardiopulmonary and Critical Care Journal (Chest), 1998, Vol. 114, pp. 1036-1041.

Margel et al: "Long-Term Intermittent Exposure to High Ambient CO2 Causes Respiratory Disturbances During Sleep in Submariners";The Cardiopulmonary and Critical Care Journal (Chest), 2003. vol. 124, pp. 1716-1723.

Muza et al: "Ventilation After Supplemental Oxygen Administration At High Altitude"; Wilderness and Environmental Medicine, 2004, vol. 15, pp. 18-24.

Van Der Mark et al: "Cancer Detection by Modulation of Respiratory O2/N2 Ratio Combined With Spectral Diffuse Optical Tomography"; Jun. 5, 2005, 8 Page Document.

Morse et al: "Carbon Monoxide and Human Disease"; Antioxidants & Redox Signaling, vol. 4, No. 2, 2002, pp. 331-338 (Plus 3 Diagrams).

Huey et al: "Limits to Human Performance: Elevated Risks on High Mountains"; The Journal of Experimental Biology 204, pp. 3115-3119 (2001), The Company of Biologists Limited, Printed in Great Britain.

Short,B.: "The Major Health Implications of Ascent to High Altitude"; ADF Health, vol. 1, Apr. 2000, pp. 73-78.

Wahrenberger, J.: "High Altitude and the Heart"; Dartmouth-Hitchcock Medical Center, 2003, 16 Page Document.

Zubieta-Calleja et al: "Acute High Altitude Hypoventilation Following Hyperoxic Tests"; High Altitude Pathology Clinic, La Paz, Bolivia, 16 Page Document.

Printout of a Series of Sessions Scheduled for a Seminar, 5693-34, 72, 73, 79, 2 Page Document, No Date.

Two Reviews of Two Lectures at the Aerospace Medical Association , Aviation, Space and Environmental Medicine, vol. 75, No. 8, Aug. 2004, p. 729.

Akin et al: "Frequency Components in Breath Holding Experiments"; Paper 5693-34, Session 7 (Photonics West, San Jose, CA) Jan. 2005.

Faris et al: "Differential Optical Measurements of the Dynamic Tissue Response to Inhaled Vasoactive Gases"; Paper 5693-72, Session 15 (Photonics West, San Jose, CA), Jan. 2005.

Colak et al: "Clinical Optical Tomography and NIR Spectroscopy for Breast Cancer Detection"; IEEE Journal of Selected Topics in Quantum Electronics, vol. 5, No. 40, Jul./Aug. 1999, pp. 1143-1158.

Gotzsche et al: "Is Screening for Breast Cancer With Mammography Justifiable"; The Lancet, vol. 355, Jan. 8, 2000, pp. 129-134.

Kamat: "Pulse Oximetry"; Indian J. Anaesth. 2002, vol. 46, (4), pp. 261-268.

Malur et al: "Comparison of Written Reports of Mammography, Sonography, and Magnetic Resonance Mammography for Preoperative Evalutation of Breast Lesions, With Special Emphasis on Magnetic Resonance Mammography"; Breast Cancer Res. vol. 3 (1), 2001, pp. 55-60.

Breast Cancer Facts & Figures 2003-2004, American Cancer Society, 2004, 27 Pages.

Breast Cancer Facts & Figures 2005, American Cancer Society, 2005, 64 Pages.

* cited by examiner

METHOD AND DEVICE FOR OPTICAL IMAGING OF A TURBID MEDIUM

The present invention relates to a method for optical imaging of a turbid medium as well as an apparatus for imaging a turbid medium.

Diffuse Optical Tomography (DOT) is an imaging technique that uses near-infrared (NIR) light and probes absorption as well as scattering properties of biological tissues. The main applications for this technique are brain imaging (e.g. stroke imaging, functional imaging—also in neonatals), optical mammography, limb and joint imaging. The technology is based on delivering low-energy electromagnetic radiation, typically through optical fibers, to the surface of the body part under investigation and measuring transmitted and/or reflected intensities at distances up to 20 cm. DOT has the benefit that the measured absorption coefficients are related to the biochemical constitution of the tissue, such as haemoglobin concentration and blood oxygenation. The technique exploits the fact that oxyhemoglobin and deoxyhemoglobin are the dominant absorbers in the near infrared region.

Diffuse Optical Tomography is especially suitable for localizing a deviant region in a turbid medium. In this context, a turbid medium is to be understood to mean biological tissue. A deviant region is to be understood to mean a region in which the turbid medium deviates in any way or form from the turbid medium in the surrounding region. More specifically, in the context of the present application such an area is to be understood to mean a region comprising tumor tissue.

Although Diffuse Optical Tomography is a promising technique, giving fast results at low costs and with high safety, a static image using a single wavelength of light with DOT does not result in a conclusive picture of the structure of the body part. Intrinsic contrast as a result of different absorption and scattering of the different tissues inside the body part is not sufficient, and image resolution is to poor to make it work. Even in the case where a number of wavelengths are used (Spectroscopic Diffuse Optical Tomography), and knowledge of the different spectral features of the different tissue types is exploited, no reliable diagnosis can be obtained with the current state of the art. Additional information to relieve this problem can be obtained, for example by using a contrast agent which enhances optical contrast on the one hand but, more importantly, opens the way to a so-called difference technique. In such a technique, the difference is taken of two or more images made before, during and after administering a contrast agent to the patient. This greatly enhances the contrast specific to the agent used because a background is subtracted, and a time sequence shows the dynamical features such as wash-in, uptake and wash-out of the contrast agent. However, administering a contrast agent has some important disadvantages, such as the need for needle injection, the costs involved and safety risks involved.

It is the aim of the present invention to provide for a method for optical imaging of a turbid medium with enhanced optical contrast, To this end the present invention provides for a method for optical imaging of a turbid medium, comprising:

a reference measurement of reference intensities of light emanating from the turbid medium at a reference blood oxygen saturation (SaO2) level in the turbid medium, and a reference imaging step for reconstructing a reference image of the turbid medium from the measured reference intensities. Said method is characterized in that it further comprises:

a contrast measurement of the contrast intensity of the light emanating from the turbid medium at a contrast blood oxygen saturation (SaO2) level in the turbid medium, and a contrast imaging step for reconstructing a contrast image of the turbid medium from the measured contrast intensities, and a comparison is made between the contrast image to the reference image of the turbid medium.

In particular, the light emanating from the turbid medium can be generated by illuminating the turbid medium with one or more light sources. Also, fluorescence from the turbid medium may cause light to emanate from the turbid medium, such fluorescence may be caused by a suitable fluorescing agent that is administered to the turbid medium in addition to the contrast measurements at different blood oxygen saturation levels.

The invention is based on the insight that—artificial—changes in blood oxygen saturation level in a turbid medium will result in dynamic changes in the optical transmission. Artificial changes in blood oxygen saturation level can e.g. be obtained by modulation of the $O_2/N_2$ ratio of a gas mixture that is administered to a human being or animal through an oxygen mask. This modulation of the $O_2/N_2$ ratio changes blood oxygenation—or oxyhemoglobin concentration—dynamically. The dynamic changes in the optical transmission can be used to obtain accurate values of, for example, blood volume using DOT imaging. Blood volume, blood oxygen saturation and blood flow in cancers appear to be different from normal tissue and therefore a greater image contrast will be obtained between the cancerous regions in a turbid medium and the normal (non-cancerous) regions in the turbid medium than the static image alone. The invention is a simple, dynamical and strongly contrast enhancing functional imaging technique using a virtual contrast agent.

When a human being holds its breath for tens of seconds, the $O_2$ level ($HbO_2$) in the blood decreases and the $CO_2$ level in the blood rises. As a result, the $CO_2$ receptors in the brainstem alarm us to breathe; we feel a strong reflex to breathe. When air containing little oxygen is breathed in, no such reflex is invoked—provided that the oxygen saturation level in the blood does not fall under 60%. Thus, it is very hard to reduce the $O_2$ level in the blood by holding our breath, but similar or much lower blood oxygen levels can be obtained by breathing a gas which contains a reduced amount of oxygen, compared to natural air. Pure nitrogen ($N_2$) is the most natural example, but helium and argon are others. In natural air we find approximately 21% of $O_2$ and 79% of $N_2$ ($O_2/N_2$ ratio is 0.26). The $O_2/N_2$ ratio could be lowered to 0.1 or less and then raised to 0.5 or more (to replenish rapidly) within a period. This will result in a dynamical enhancement of the $Hb/HbO_2$ contrast which can be measured by Spectral DOT.

The advantages of the method according to the present invention are clear. First of all it provides a contrast enhancing functional imaging method. The $O_2/N_2$ mixtures are cheap and easy to obtain and the wash-in and wash-out is very rapid. Furthermore no interventional steps such as needle injection or infusion of any contrast agent are required.

In an advantageous embodiment the method for optical imaging of a turbid medium according to the present invention comprises the following steps:

several contrast measurements are made to measure respective sets of reference light intensities emanating from the turbid medium at the contrast blood oxygen saturation level;

several reference images and several contrast images are reconstructed from the sets of reference light intensities and from the sets of contrast light intensities, respectively and the comparison is made of the several contrast images to the several reference images.

In an advantageous embodiment an average reference image is formed by averaging of the several reference images, an average contrast image is formed by averaging of the several contrast images and the comparison is made between the average contrast reference image and the average reference image.

By making several reference and contrast images and averaging these images the signal to noise ratio can be improved.

Preferably, the comparison between the average contrast reference image and the average reference image involves subtraction or taking the ratio of the (average) contrast image and the (average) reference image.

The blood oxygen saturation level in the turbid medium is preferably modulated by modulating the ratio of the partial oxygen pressure ($pO_2$) to the partial nitrogen pressure ($pN_2$) administered to the subject to be examined.

For example, in case of a human being, the administration of oxygen and nitrogen in de desired ratio can take place by making the human being breath through an oxygen mask through which the oxygen/nitrogen gas mixture is supplied.

During the Spectral DOT imaging procedure, the partial pressure $O_2/N_2$ ratio in the could be lowered to, say 0.1 or less and then raised to, say 0.5 or more (to replenish rapidly) within a period, and this sequence could be repeated to obtain better signal to noise ratio (SNR). Notably, the SNR is improved by averaging over several measurements Note further that averaging and subtraction can be done either on the measured light intensities or on the reconstructed images. Because of the intrinsic nonlinear character of the image reconstruction process these two possibilities are not equivalent, but do serve the same aim. In contrast to this, the operations of averaging and subtraction are commutative and hence can be done in reverse order without consequences to the result. This will result in a dynamical enhancement of the $Hb/HbO_2$ contrast which can be measured by Spectral DOT. Hart rate, blood pressure and respiration should be monitored tightly and are obvious candidates to be used as feedback signals on both the duration and amplitude of the oxygen modulation period.

In an example of the invention the blood oxygen saturation level is modulated by modulating the ratio of the partial oxygen pressure and partial nitrogen pressure. This achieves that that ambient (e.g. atmospheric pressure) in which the patient to be examined does not need to be changed.

Preferably the $O_2/N_2$ ratio in the turbid medium is modulated by administering the concerned human being or animal $O_2/N_2$ in a ratio that is higher or lower than 0.26. A ratio higher than 0.26 will result in a high concentration of oxyhemoglobin, while a ratio lower than 0.26 will result in a higher concentration of deoxyhemoglobin.

The oxygen or nitrogen or oxygen/nitrogen mixture can be administered to the human being or animal concerned in several ways. A preferable way is, however, that administering via a mouth-breathing mask, in particular when human beings are involved.

The invention also pertains to an apparatus for imaging a turbid medium. The apparatus has the functionality to carry out the method of the invention. An example of such an apparatus is an imaging system for optical or notably near-infrared imaging of a woman's breast. Imaging of this kind of turbid medium, notably human biological tissue is possible in a wavelength range of 50 nm to 1.4 µm, very good results are achieved in the wavelength range of 650-900 nm and excellent results are achieved in the range of 700-800 nm. The choice of wavelength ranges depends on consideration of low scatter (i.e. which increases at shorter wavelength) low absorption (which increases at high wavelength) and the absence of particular absorption bands due to e.g. oxygenated or non-oxygenated blood, etc. It has appeared that the breast tissue optically behaves as turbid because of multiple scatter of the light that progresses through the breast tissue. The imaging apparatus of the invention comprises an examination space to receive the turbid medium. In practice the examination space for example has the form of a chamber that is open at it upper end and into which the woman's breast be suspended from above into the opening of the chamber while the woman is comfortably positioned face down (that is, in prone position) over the chamber. Often a matching fluid is applied to surround the breast suspended into the chamber to avoid strong optical transitions at the edge of the breast. The use of the matching fluid strongly reduced arifacts in the reconstructed image of the breast being examined.

Electro-magnetic radiation from the breast is measured by electro-magnetic radiation detection modules located at or near the walls of the chamber. Alternatively, one or several electro-magnetic radiation detection modules may orbit around the examination space. The electro-magnetic radiation detection modules detect electro-magnetic radiation from the examination space from several orientations. In one aspect of the imaging apparatus the breast may be illuminated by sources that are located around the examination space or that orbit around the examination space in order to irradiate the turbid medium, i.e. the woman's breast, from several orientations. In another aspect of the imaging apparatus of the invention a contrast agent is administered to the patient to be examined which cause fluorescence from the breast tissue, where notably fluorescence is enhanced in tumor tissue. For example the fluorescence enhancement is due to increased concentration of contrast agent that is due to preferred accumulation of contrast agent in tumor tissue.

The imaging apparatus of the invention is provided with one or more electro-magnetic radiation detection modules. The electro-magnetic radiation detection modules are employed in the imaging apparatus of the invention to detector electro-magnetic radiation, notably optical or near-infrared radiation from the turbid medium, notably the woman's breast. These one or more electro-magnetic radiation detection modules supply output intensity signals that represent the accumulated electrical charges that in turn are representative of the radiation intensities as observed from respective orientations from the examination zone. These output intensity signals are applied to a reconstructor which reconstructs one or several images of the turbid medium, i.e. the woman's breast. Several reconstructions algorithms are available for reconstructing two-dimensional or three-dimensional image datasets.

Further, the invention pertains to a computer program. The computer program of the invention may be provided on a data carrier such as a CD-Rom, and may also be downloaded from a data network, like the world-wide web. The computer program may be installed in the processor of an apparatus for optical imaging a turbid medium, such as a DOT imaging apparatus. Having the computer program of the invention installed provides the apparatus for optical imaging a turbid medium with the functionality to carry out the method of the present invention.

Figure 2:
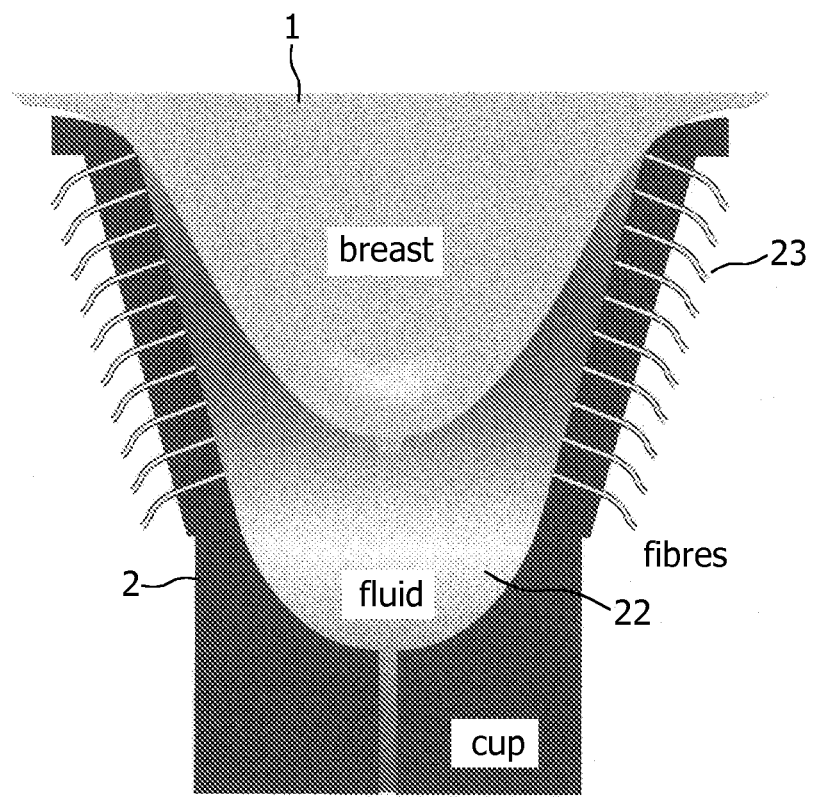
Figure 3:
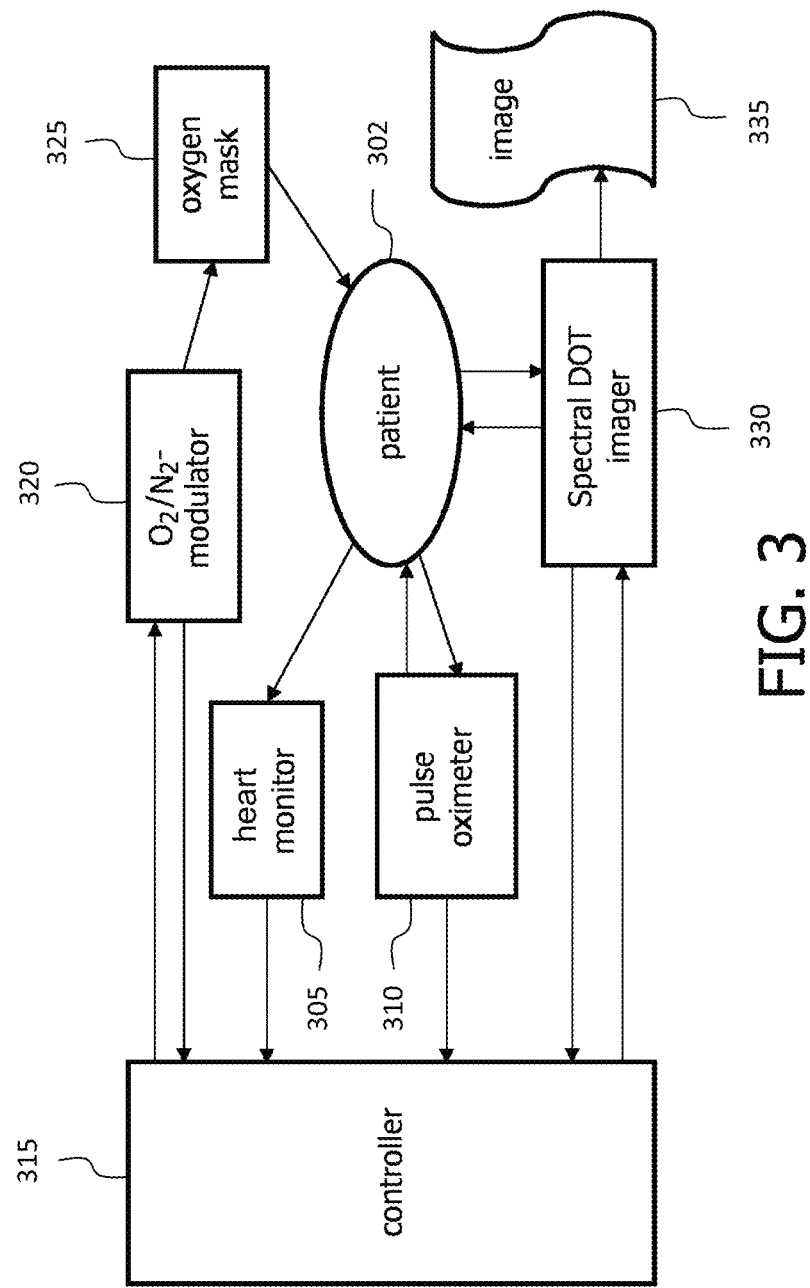

These and other aspects of the invention will be elucidated with reference to the embodiments described hereinafter and with reference to the accompanying drawing wherein FIG. 1 shows a schematic diagram of the apparatus for imaging a turbid medium of the invention;

FIG. 2 shows a schematic cross-sectional drawing of the cup with a turbid medium in the form of a breast; and FIG. 3 shows a schematic diagram of a system according to the present invention comprising a near-infrared imager and a system for administering respiratory gases.

FIG. 1 shows a schematic diagram of the apparatus for imaging a turbid medium of the invention. Notably, the apparatus for imaging a turbid medium shown diagrammatically in FIG. 1 is an optical mammography system. The optical mammography system comprises a carrier 11 on which the patient to be examined (notably a woman whose breast(s) 1 are to be examined is placed in prone position (i.e. face down) having one breast suspended in an examination space that has the form of a measurement cup 2 (see FIG. 2). The space between the breast 1 and the cup surface is filled with a scattering fluid 22, which scattering properties for example closely match the scattering properties of the average breast so that transitions of optical properties between the breast tissue and space outside the breast are reduced.

FIG. 2 shows a schematic cross-sectional drawing of the cup with a breast 1.

A large number of fibres 23 (510 in total) is connected with one end to the cup. Half of the fibres are connected to detector modules 5 with the other end, and half of the fibres are connected to a fibre-switch 12 with the other end. The fibre-switch 12 can direct light from multiple lasers with different wavelengths 24 in either one of the 256 source fibres 23 (255 to the cup, one directly to a detector fibre). In this way, either one of the source fibres 23 can provide a conical light beam in the cup. By properly switching the fibre-switch 12, all the source fibres will emit a conical light beam subsequently.

The light from the selected source fiber is scattered by the scattering fluid and the breast, and is detected by the 255 detector modules. The scattering of light in breast tissue is strong, which means that only a limited amount of photons can transverse the breast, compared to the reflected (or back-scattered) light. Therefore, a large dynamical range should be covered by the detectors (about 9 orders of magnitude). Photodiodes are used as photosensors 4 in the detector modules. The front-end detector electronics includes of these photodiodes and an amplifier 3. The amplification factor of the amplifier can be switched between several values. The machine first measures at the lowest amplification, and increases the amplification if necessary. The detectors are controlled by a computer 14.

This computer 14 also controls the lasers, the fibre-switch, and the pump system. The computer, cup, fibres, detectors, fibre-switch, and the lasers are all mounted into a bed as shown in FIG. 2.

A measurement starts with a cup 2 filled completely with the scattering fluid 22, this is the calibration measurement. After this calibration measurement, a breast 1 is immersed in the fluid, and the measurement procedure is carried out again. Both the calibration and the breast measurement consist of 255×255 detector output intensity signals (OIS) for each of the three lasers 24. These detector output intensity signals (OIS) can be converted into a three dimensional image using a process called image reconstruction. The image reconstruction of the image of the breast is carried out by a reconstructor that is usually implemented in software in the computer 14. The reconstruction process, which is based on for example an algebraic reconstruction technique (ART) or finite element method (FEM), finds the most likely solution to the (ill-posed) inverse problem.

FIG. 3 shows a schematic diagram of a system comprising a Near Infrared imager 300 that can make images at multiple wavelengths (spectral DOT imager) of, for example, the breast of patient 302. The heart rate and blood oxygenation level are monitored by heart monitor 305 and pulse oximeter 310, respectively. The signals are send to a controller 315 and the controller 315 sends signals to a set of gas valves and receives readings from pressure gauges in an O2/N2-modulator 320 in order to adjust the O2/N2 gas mixture. The gas mixture is send to the patient using a mouth-breathing mask or anesthetic oxygen mask 325. A spectral DOT imager 330 receives control signals about the gas mixture and it sends signals to the controller 315 about its own status, such as the progress on the image scan. The output, amongst others, is a functional image 335 of blood supply and blood oxygenation in the patient 302. These data can subsequently be used to mark locations suspicious to cancer development.

The invention claimed is:

1. A method for optical imaging of a turbid medium present in a human subject, the method comprising:
    measuring reference intensities of light emanating from the turbid medium while an $O_2/N_2$ gas mixture is supplied to the human subject and while the $O_2/N_2$ gas mixture has a reference ratio of partial oxygen pressure ($pO_2$) to partial nitrogen pressure ($pN_2$);
    reconstructing a reference image of the turbid medium from the measured reference intensities;
    measuring contrast intensities of the light emanating from the turbid medium while the $O_2/N_2$ gas mixture is supplied to the human subject and while the $O_2/N_2$ gas mixture has a contrast ratio of partial oxygen pressure ($pO_2$) to partial nitrogen pressure ($pN_2$);
    reconstructing a contrast image of the turbid medium from the measured contrast intensities; and
    comparing the contrast image of the turbid medium to the reference image of the turbid medium,
    wherein the reference ratio is different from the contrast ratio.

2. The method of claim 1, wherein the turbid medium is irradiated by light from source plurality of optical fibers to generate the reference intensities and the contrast intensities of the light emanating from the turbid medium.

3. The method of claim 1, wherein comparing the contrast image of the turbid medium to the reference image of the turbid medium comprises subtracting the reference image from the contrast image.

4. The method of claim 1, wherein one of the reference ratio and the contrast ratio is greater than 0.26 and another of the reference ratio and the contrast ratio is less than 0.26.

5. A method according to claim 1, wherein the $O_2/N_2$ gas mixture is administered via a gas mask.

6. The method of claim 1, wherein the reference ratio and the contrast ratio are each in a range from 0.1 to 0.5.

7. The method of claim 1, wherein the reference image is an average reference image generated from a plurality of measurements of the reference intensities of light emanating from the turbid medium at while the $O_2/N_2$ gas mixture has the reference ratio, and wherein the contrast image is an average contrast image generated from a plurality of measurements of the contrast intensities of light emanating from the turbid medium at while the $O_2/N_2$ gas mixture has the contrast ratio.

8. An apparatus for optical imaging of a turbid medium present in a human subject, the apparatus comprising:
    an $O_2/N_2$-modulator configured to supply an $O_2/N_2$ gas mixture to the human subject and to modulate a ratio of partial oxygen pressure ($pO_2$) to partial nitrogen pressure ($pN_2$) in the $O_2/N_2$ gas mixture;
    one or more detector modules configured to detect light emanating from the turbid medium when the $O_2/N_2$-modulator causes the $O_2/N_2$ gas mixture to have a reference ratio of partial oxygen pressure (pO$_2$) to partial nitrogen pressure (pN$_2$), and to detect light emanating from the turbid medium when the O$_2$/N$_2$-modulator causes the O$_2$/N$_2$ gas mixture to have a contrast ratio of partial oxygen pressure (pO$_2$) to partial nitrogen pressure (pN$_2$), wherein the reference ratio is different than the contrast ratio;

a processor configured to reconstruct a reference image from an output of the one or more detector modules when the O$_2$/N$_2$ gas mixture has the reference ratio, and to reconstruct a contrast image from an output of the one or more detector modules when the O$_2$/N$_2$ gas mixture has the contrast ratio; and a comparator module configured to carry-out a comparison between the contrast and reference images.

9. The apparatus of claim 8, wherein the reference ratio and the contrast ratio are each in a range from 0.1 to 0.5.

10. A tangible non-transitory data carrier having stored thereon computer programming instructions for causing a processor to execute an algorithm, comprising:

measuring reference intensities of light emanating from the turbid medium of a human subject while an O$_2$/N$_2$ gas mixture is supplied to the human subject and while the O$_2$/N$_2$ gas mixture has a reference ratio of partial oxygen pressure (pO$_2$) to partial nitrogen pressure (pN$_2$);

reconstructing a reference image of the turbid medium from the measured reference intensities;

measuring contrast intensities of the light emanating from the turbid medium while the O$_2$/N$_2$ gas mixture is supplied to the human subject and while the O$_2$/N$_2$ gas mixture has a contrast ratio of partial oxygen pressure (pO$_2$) to partial nitrogen pressure (pN$_2$); and reconstructing a contrast image of the turbid medium from the measured contrast intensities, and comparing the contrast image of the turbid medium to the reference image of the turbid medium, wherein the reference ratio is different from the contrast ratio.

* * * * *